United States Patent [19]

Prather et al.

[11] Patent Number: 4,994,384
[45] Date of Patent: Feb. 19, 1991

[54] MULTIPLYING BOVINE EMBRYOS

[75] Inventors: Randall S. Prather; Frank Barnes, both of Madison, Wis.; James Robl, Belchertown, Mass.; Neal L. First, Madison, Wis.; Vincent F. Simmon, Potomac, Md.

[73] Assignee: W. R. Grace & Co.-Conn., New York, N.Y.

[21] Appl. No.: 113,791

[22] Filed: Oct. 27, 1987

Related U.S. Application Data

[63] Continuation-in-part of Ser. No. 948,269, Dec. 31, 1986, abandoned.

[51] Int. Cl.$^5$ ............................................. C12N 15/00
[52] U.S. Cl. .................................... 435/172.2; 800/2; 800/DIG. 6; 435/172.3; 935/53; 935/111
[58] Field of Search ......................... 435/172.3, 172.2; 935/53, 111; 800/1, 2, DIG. 6

[56] References Cited

U.S. PATENT DOCUMENTS 3,906,929  9/1975  Augspurger.
4,664,097  5/1987  McGreth et al. .................. 128/1 R

OTHER PUBLICATIONS

Lohse et al., Theriogenology 23(1):205 (1985).
Loskutoff et al., Theriogenology 25(1):168 (1986).
Robl et al., "Nuclear Transplantation in Bovine Embryos," *Theriogenology,* 25(1):189 (1986).
Waddington et al., "Transplantation of Nuclei in Newt's Eggs," *Nature,* 172:1050-1051 (1953).
Willadsen, "Nuclear Transplantation in Sheep Embryos," *Nature,* 320:63-65 (1986).
Illmensee et al., "Nuclear Transplantation in *Mus Musculus:* Developmental Potential of Nuclei from Preimplantation Embryos," *Cell* 23:9-18 (1981).
King, "Nuclear Transplantation in Amphibia,"[Methods Cell Biol., 2:1-35 (1966).
McGrath et al., "Nuclear Transplantation in the Mouse Embryo by Microsurgery and Cell Fusion," *Science,* 220:1300-1302 (1983).
Prather et al., "Multiplication of Bovine Embryos," (abstract), Biol. Reprod. 34 (Suppl. 1):192 (1986).
Robl, et al., "Manipulation of Gametes and Embryos in the Pig," *Jour. Reprod. Fert.* (Suppl) 33:101-114 (1985).
Briggs et al., "Transplantation of Living Nucleu from Blastula Cells into Enucleated Frogs's Eggs," Zoology 38:455-463 (1952).
Briggs et al., "Transplantation of Nucleu of Various Cell Types from Neurulae of the Mexican Axolotl (*Ambystoma mexicanum*), " *Develop. Biol.,* 10:233-246 (1964).
Comandon et al., "Greffe Nucleaire Totale, Simple ou Multiple, Chez une Amibe," *Comp. Rend. Soc. Biol.,* 130:744-748 (1939).
Elsdale et al., "A Description of the Technique for Nuclear Transplantation in *Xenopus laevis,*" *Jour. Embryo. Exp. Morph.,* 8(4):437-444 (1960).

*Primary Examiner*—Charles F. Warren
*Assistant Examiner*—Jasemine C. Chambers
*Attorney, Agent, or Firm*—Jill H. Krafte

[57] ABSTRACT

A method of multiplying bovine embryos by transfer of nuclei is described. The method includes enucleating a recipient oocyte, transferring the donor embryo nucleus to the enucleated recipient oocyte, and fusing the donor nucleus to the recipient oocyte by dielectrophoresis. The method is intended to allow the generation of multiplied genetically identical cattle.

23 Claims, No Drawings 4,994,384

MULTIPLYING BOVINE EMBRYOS

This is a continuation-in-part of copending U.S. Ser. No. 948,269, filed on Dec. 31, 1986, now abandoned.

FIELD OF THE INVENTION

The present invention is generally directed to a process for multiplying bovine embryos and specifically directed to a process for transplanting the nuclei of donor bovine embryos into enucleated recipient oocytes, that is, oocytes from which the nuclei have been removed.

DESCRIPTION OF THE PRIOR ART

Advanced genetic improvement and selection techniques continue to be sought in the field of animal husbandry. With specific reference to dairy cattle, for example, significant increases in milk production have been made with the wide scale use of genetically superior sires and artificial insemination. Dairy cows today produce nearly twice as much milk as they did 30 years ago. Further genetic improvement can be accomplished by the multiplication of superior or genetically manipulated embryos by cloning.

It has now become an accepted practice to transplant embryos in cattle to aid in the production of genetically superior stock. The cloning of embryos together with the ability to transplant the cloned embryos makes it possible to produce multiple genetically identical animals. Bovine embryos may currently be cloned only by surgical bisection of a developing embryo, however, and the number of clones which can be produced by this method is limited to two to four before the bisected embryos become non-viable. Nuclear transplantation from a multi-cell embryo to a plurality of embryonic single cells offers the potential of overcoming this limitation and would enable the production of large numbers of multiplied identical animals.

Nuclear transfer was first accomplished in *Amoeba sphaeronucleus* in 1939 by Comandon and de Fonbrune ("Greffe Nucleaire Totale, Simple ou Multiple, Chez une Amibe," *Soc. Biol.* 130:744, 1939). This was followed in 1952 by successful nuclear transfer in *Rana pipiens* by Briggs and King ("Transplantation of Living Nuclei from Blastula Cells into Enucleated Frogs' Eggs," *Zoology* 38:455-463, 1952). The procedure for successful nuclear transfers, according to Briggs and King (*supra*), included the following:

(1) the activation of a recipient oocyte;
(2) enucleation, the process of removing or inactivating the chromosomes from the recipient oocyte; and
(3) transfer of a whole lysed blastomere (a cell resulting from embryo cleavage prior to gastrulation), with a nucleus, from a blastula or early gastrula stage embryo back to the enucleated oocyte.

Elsdale et al. ("A Description of the Technique for Nuclear Transplantation in *Xenopus laevis*," *J. Embryol. exp. Morph.* 8(4):437-444, 1960), utilized ultraviolet irradiation to, in one step, inactivate the egg pronucleus and activate the unfertilized oocyte. In the axolotl, activation was reported by electrical shock with chromosomes of the egg nucleus being eliminated by ultraviolet irradiation, (Briggs, R., et al., "Transplantation of Nuclei of Various Cell Types from Neurulae of the Mexican Axolotl (*Ambystoma mexicanum*)," *Develop. Biol.* 10:233, 1964). Transfer of a whole lysed blastomere containing a nucleus into the enucleated oocyte via a small bore micropipette was the common method of nuclear transfer for all these techniques.

Two techniques have been used for nuclear transfer in the mouse. Illmensee and Hoppe used a totally surgical method in which a micropipette was inserted through the plasma membrane and into the cytoplasm of a pronuclear stage embryo for nuclear removal and insertion (Ilmensee, K. and Hoppe, P. C., "Nuclear Transplantation in *Mus musculus*: Developmental Potential of Nuclei from Preimplantation Embryos," *Cell* 23:9, 1981). McGrath and Solter reported a nondisruptive method of transplanting nuclei (McGrath, J. and Solter D., "Nuclear Transplantation in the Mouse Embryo by Microsurgery and Cell Fusion," *Science* 220:1300, 1983). Nuclei were removed as membrane bounded pronuclear karyoplasts without penetrating the plasma membrane of the embryo. The nucleus was inserted into a recipient cell by cell fusion, using Sendai virus as the fusigenic agent. A small volume of Sendai virus suspension was aspirated after removal of the donor nucleus and the virus suspension and the pronuclear karyoplasts were injected sequentially into the perivitelline space of the recipient embryo. At best, the microsurgical method of Illmensee and Hoppe (supra) was about 30-40% efficient, whereas the nondisruptive method of McGrath and Solter (supra) was greater than 90% efficient. These techniques have been successful in producing blastocyst stage embryos which do not continue development to term. Reports that Illmensee and Hoppe produced three live mice have been questioned.

It was later reported that blastocyst stage embryos and mice were produced by transferring nuclei into enucleated pronuclear zygotes only when the donor cell stage was also pronuclear or at a very early two-cell stage (McGrath, J. and Solter, D., "Inability of Mouse Blastomere Nuclei Transferred to Enucleated Zygotes to Support Development *In Vitro*," *Science* 226:1317-1319, 1984; Surani, M. A. H. et al., "Nuclear Transplantation in the Mouse: Heritable Differences Between Paternal Genomes after Activation of the Embryonic Genome," *Cell*, 45:127-136, 1986; and Robl, J. M. et al., "Nuclear Transplantation in Mouse Embryos: Assessment of Recipient Cell Stage," *Biol. Reprod.* 34:733-739, 1986).

Recently, a method for nuclear transplantation in sheep was reported (Willadsen, S. M., "Nuclear Transplantation in Sheep Embryos," *Nature* 320:63-65, 1986) which describes the use of dielectrophoresis for activation and fusion, and the use of metaphase II oocytes as recipients. These experiments resulted in the birth of cloned lambs. However, to date no prior art publications are known to exist on methods for nuclear transfer in the bovine.

SUMMARY OF THE INVENTION

It is thus an object of the present invention to provide a useful process for cloning bovine embryos.

It is another object of the present invention to provide a process for cloning bovine embryos by nuclear transfer.

It is still further an object of the present invention to provide a process for transplanting the nucleus or a whole blastomere with its nucleus from a donor bovine embryo to an enucleated recipient bovine oocyte. It is a related object to use the process for the generation of multiplied genetically identical cattle.

These and other objects will become more apparent from the following detailed description and appended claims.

The present invention is directed to a process for transplanting nuclei in bovine embryos. The nuclei are removed from the donor bovine embryo without penetrating the plasma membrane and are inserted into recipient oocytes by electrically induced cell fusion.

The nuclear transfer process involves removing the nucleus from the recipient oocyte, introducing the membrane-bounded nucleus of the donor embryo cell into the perivitelline space of the enucleated recipient oocyte, orienting the respective plasma membranes of the donor membrane-bounded nucleus and enucleated recipient oocyte, and electrically inducing activation of the oocyte and fusion of the donor membrane-bounded nucleus into the enucleated recipient oocyte. The conditions of the oocyte at activation and the manner in which the activation and fusion steps are performed are critical to successful nuclear transfer of donor cells or nuclei into enucleated bovine oocytes.

DETAILED DESCRIPTION OF INVENTION

The present invention is directed to a series of steps which collectively result in the cloning of bovine embryos by nuclear transplantation. The procedure includes a non-disruptive method of removing the nucleus from the recipient oocyte and isolating a nucleus from a donor embryo, bounded by a membrane, either by removal of the nucleus from the donor cell or by isolating a blastomere itself. The donor nucleus is then joined to the recipient oocyte and electrically induced cell fusion is used to introduce the nuclei from the donor embryo cell into a recipient cell. The bovine embryo cloning process follows a basic five step procedure as follows:

(1) selecting a proper recipient embryo or oocyte for nuclear transfer;
(2) enucleating, i.e., removing the nuclear material from the recipient oocyte;
(3) introducing the membrane-bounded nucleus of the donor embryo to the enucleated recipient oocyte;
(4) orienting the donor membrane-bounded nucleus and the recipient oocyte for cell fusion; and
(5) fusing the membrane surrounding the donor nucleus to the membrane of the recipient oocyte and activating the recipient oocyte by dielectrophoresis.

The overall procedure disclosed herein may be described as cloning or as multiplication of embryos (and cattle) by nuclear transfer, for the production of multiple genetically identical embryos, and ultimately, animals.

The "oocyte," as used here for the recipient cell, means a cell which develops from an oogonium and, following meiosis, becomes a mature ovum. It has been found that not all oocytes are equally optimal cells for efficient nuclear transplantation in the bovine. For purposes of the present invention, metaphase II stage oocytes, matured either in vivo or in vitro, have been found to be optimal. Mature metaphase II oocytes may be collected surgically from either nonsuperovulated or superovulated cows or heifers 35 to 48 hours past the onset of estrus or past an injection of human Chorionic Gonadotropin (hCG) or similar hormone. Alternatively, immature oocytes may be recovered by aspiration from ovarian follicles obtained from slaughtered cows or heifers and then may be matured in vitro by appropriate hormonal treatment and culturing.

The donor cell embryos may be obtained by flushing from surgically recovered oviducts or may be nonsurgically flushed from the uterus in manners known to the art. The stage of development of the donor embryos should be from the two-cell to thirty-two cell stage, i.e., prior to significant cellular differentiation. Donor embryos at the sixteen to thirty-two cell stage are sometimes referred to as morula rather than blastula. Nevertheless, the term blastula will be used herein to refer to the embryo and the term blastomere will be used to refer to a single cell from any such embryo prior to gastrulation.

The nucleus of the donor cell should be membrane-bounded to be used optimally in this procedure. Such a membrane-bounded nucleus may either consist of an entire blastomere or may consist of a karyoplast, which is an aspirated cellular subset including a nucleus and a small amount of cytoplasm bounded by a plasma membrane.

Micromanipulation of the bovine cells is performed in a manner similar to the methods of McGrath and Solter (supra), which is incorporated herein for details of the micromanipulation technique. Micromanipulation is performed using a cell holding pipette, having an outer diameter of about 120 micrometers and an inner diameter of approximately 25 to 35 micrometers, and a beveled, sharpened enucleation and transfer pipette having an outer diameter of approximately 25 to 35 micrometers. Mature oocytes should be first treated with cytochalasin B at about 7.5 micrograms per milliliter, or an effectively similar microtubal inhibitor at a concentration sufficient to allow the enucleation and transfer pipette to be inserted through the zona pellucida to allow for removal of a portion of the cytoplasm without, at any point, actually rupturing the plasma membrane. The mature oocyte is first held in place by mild suction by the cell holding pipette. The enucleation and transfer pipette is then inserted through the zona pellucida of the oocyte at the point of either the metaphase II bulge or adjacent to the first polar body, i.e., in a location intended to be adjacent to the metaphase chromosomes. The pipette does not penetrate the plasma membrane. Aspiration applied through the pipette draws a cellular bulge into the pipette which includes, in the case of the metaphase II bulge, the entire bulge and surrounding cytoplasm, or, in the case of the first polar body, the polar body plus the surrounding cytoplasm. This process is intended to draw all the metaphase chromosomes into the pipette. As the pipette is withdrawn, with suction maintained, the plasma membrane is stretched and then seals to itself leaving a competent plasma membrane on the enucleated oocyte.

The donor embryos may be treated with cytochalasin B, or may not be, depending on the size of the transfer pipette. When using a pipette of less than 30 microns, treatment is recommended to prevent rupture of the blastomere. The nuclei of the donor embryo cells are transferred either by aspirating a part of the blastomere which contains the nucleus, thus creating a karyoplast, or by aspirating the entire blastomere. Aspirating the entire cell is preferred. The transfer pipette carrying the aspirated membrane-bounded nucleus is then inserted through the zona pellucida of the recipient enucleated oocyte, and the membrane-bounded nucleus is deposited under the zona pellucida with its membrane abutting the plasma membrane of the recipient oocyte.

Fusion of the membrane-bounded nucleus to the enucleated recipient oocyte and simultaneous activation of the recipient oocyte are carried out by a single dielectrophoresis step using commercially available electrofusion equipment which is described below. Prior to electrofusing the donor embryo nucleus and enucleated recipient oocyte together, it is necessary to orient the cell membranes in the electric field. The term "orientation" as used herein is defined as the placement of the two cells such that the plane of contact of the two membranes, i.e., the plasma membrane of the body carrying the donor nucleus and the plasma membrane of the recipient oocyte, which will become fused together, is perpendicular to the electrical field. It has been found that random orientation results in a marked reduction in the successful fusion rate. If cells are oriented such that the fusion membranes are parallel, or at approximately a 45° angle, to the electrical field, the rate of successful fusion will decrease. The alignment may be done electrically or mechanically. If the size of the two cells is not greatly disproportionate, a small alignment alternating-current voltage ($\sim 5$ volts per millimeter at 1000 KHz) for a short time (10 seconds) will cause the cells to reorient with their membranes apposed. Repeated pulses may be needed. If the cells vary greatly in size, mechanical manipulation may be required to properly orient the membranes.

The actual insertion of a membrane-bounded nucleus into an enucleated bovine oocyte is conducted by a dielectrophoretic method of cell fusion, using a DC current and using a non-conductive, i.e., non-ionic, cell fusion medium such as a mannitol solution or Zimmerman cell fusion medium. The fusion phenomenon is the result of cell membrane breakdown and pore formation between properly oriented opposing cells. The pores, or small channels, created between the two cells are thermodynamically unstable because of the high surface curvature of the channels and the associated high tension in the membrane. This instability causes the channels to merge and enlarge until the membranes form a single cell.

The embryonic single-celled clones produced as described herein preferably are cultured, either in vivo or in vitro, to the morula or blastula stage. For example, the clones may be cultured in sheep oviducts or in a suitable culture medium. The embryos then may be transplanted into the uteri of cattle, or other suitable animals, at a suitable stage of estrus. The procedures for transplantation are commonly known and practiced in the embryo transplant field. A percentage of these transplants will initiate pregnancies in the maternal surrogates. Live calves born of these pregnancies will be genetically identical where the donor cells were from a single embryo or a clone thereof.

The following examples are offered by way of illustration and not by way of limitation.

EXPERIMENTAL PROCEDURES

Source of Embryos. Metaphase-stage oocytes and later stage bovine donor embryos were obtained from the oviducts of non-superovulated or superovulated slaughtered cows or heifers at 36 to 108 hours after the onset of estrus. The animals were preferably synchronized with two injections (total 2 cc) of cloprostenol sodium ("Estrumate," reg. TM of Miles Laboratories, Shawnee, Kans.) and superovulated with a four day treatment of 40 mg FSH-P (Schering Corp., Omaha, Nebr.). The nuclear transplant experiments utilized metaphase II stage recipient oocytes matured in vivo or in vitro as recipients, and 2-cell to 32-cell stage embryos as donors.

Embryo Handling and Micromanipulation. Embryos were recovered and manipulated in a TL Hepes buffered modified Tyrodes medium prepared according to Bavister et al., "Development of Preimplantation Embryos of the Golden Hamster in a Defined Culture Medium," *Biol. Reprod.*, 28:235, 1983). The embryos were placed in a medium containing cytochalasin B (7.5 micrograms/ml) ten minutes before and during micromanipulation. Demicolcine (0.1 micrograms/ml) was also added to the medium. For testing cell fusion conditions in the bovine, a small cytoplast was removed from the recipient oocyte then reinserted into the perivitelline space. For nuclear transplantation, pronuclear recipient embryos were first centrifuged in a procedure according to Wall et al., ("Development of Porcine Ova that were Centrifuged to Permit Visualization of Pronuclei and Nuclei," *Biol. Reprod.* 32:645, 1985) at 15,000 G for 3 min to allow visualization of the pronuclei.

Recipient oocytes were enucleated by aspirating approximately one-half the cytoplasm juxtaposed to the polar body using a 25–35 micron transfer pipette, leaving an enucleated membrane-bounded oocyte. Nuclei from later stage donor embryos were removed by aspirating the nucleus and some surrounding membrane-bounded cytoplasm from a blastomere or by aspirating an entire blastomere. Micromanipulation was conducted using a holding pipette having an outer diameter of approximately 120 microns and an inner diameter of approximately 30 microns and a beveled, sharpened enucleation and transfer pipette having an outer diameter of approximately 25 to 35 microns. Whole blastomeres, containing nuclei, were removed from donor embryos and inserted into the perivitelline space of the recipient oocytes by the method of McGrath and Solter (supra).

In those embryos in which development in vitro was to be monitored, embryos were placed in 50 microliter drops of modified Tyrodes medium under paraffin oil in a humidified 5% $CO_2$ in air atmosphere at 97.5° C. Development of the embryos in sheep oviducts also was monitored. Embryos were placed in agar blocks then transferred to sheep oviducts which were ligated above the tubo-uterine junction. At five days following transfer the embryos were recovered and development was assessed. Developmental potential was further tested in two embryos by transferring to a recipient cow.

Cell Fusion. A fusigenic virus method (using two different viruses) and an electrofusion method were tested for fusion of the donor and recipient embryo cells prepared as described herein. Sendai virus was grown and inactivated by the method of Giles and Ruddle ("Production of Sendai virus for cell fusion," In vitro 2:103, 1973). The titer of Sendai virus was between 6400 and 9600 hemagglutinating units/ml as tested on guinea pig red blood cells. This virus gave greater than 90% fusion in concomitant mouse embryo nuclear transplant experiments. The other virus that was tested was bovid herpevirus 1 (NY1 Strain) obtained from G. J. Letchworth (Letchworth and LaDue, "Bovine Herpes Mammillitis in Two New York Dairy Herds," *J. Amer. Vet. Med. Assoc.* 180:902, 1982). The bovid herpes virus had an approximate titer of $10^7$ $TCID_{50}$/ml and was concentrated 100x. This virus readily causes cell fusion in bovine tissue culture cells. Both viruses were used as described by McGrath and Solter (supra). In attempting to fuse cytoplasts to mature bovine embryos, no success was achieved using the fusigenic viruses. Accordingly, all future fusion trials were accomplished using electrofusion.

Two types of media, TL Hepes and Zimmerman Cell Fusion Medium (GCA Corporation, Chicago, IL), were compared for their effect on fusion rate. Cells from embryos were washed in the medium then placed in the fusion chamber with the appropriate medium. Following the fusion treatment, oocytes were placed in modified Tyrodes medium, in 50 microliter drops, under paraffin oil in a humidified 5% $CO_2$ in air incubator and monitored periodically for fusion.

Activation and fusion of the intact, membrane-bounded nuclei to the enucleated oocytes were carried out in Zimmerman Cell Fusion Medium by dielectrophoresis using a Zimmerman Electrofusion Instrument, GCA Corporation, Chicago, Ill. The fusion chamber consisted of two parallel electrodes 1 mm apart on a glass slide. The instrument was adjusted in the following manner:

Fusion voltage: 100-120 volts (DC)
Electrode distance: 1 mm
Alignment voltage: 1-5 volts (AC)
Alignment frequency: 1000 KHz
Pulse duration: 10-40 microseconds
Postfusion alignment time: 5 seconds The alignment pulse proved largely unsuccessful in aligning small blastomeres or karyoplasts placed adjacent the membrane of the recipient oocyte in bovine cells. Therefore, the alignment was largely done mechanically. The membrane-bounded nucleus, i.e., blastomere or karyoplast, and enucleated oocyte were aligned mechanically using a holding pipette so that the fusion pulse would pass perpendicularly through the interface of the membrane bounding the nucleus and enucleated oocyte membrane. The embryos were then cultured in vitro for 18-24 hours in 50 microliter drops of modified Tyrodes medium, then were placed in agar blocks for transfer to the ligated oviduct of a recipient mother such as, for example, a ewe.

EXAMPLE 1

The effect of cell orientation on the rate of fusion was initially tested with two-cell mouse embryos. Donor membrane-bounded nuclei and oocytes were aligned with an alternating current pulse of 1000 KHz and up to 5 volts. Following alignment, the cells were exposed to a direct current fusion pulse of 100 volts for 20 microseconds. In fusing bovine cells it was found that the small size of the donor cell did not give the cells sufficient polarity to allow alignment by an alternating current pulse. Therefore, the cells were aligned mechanically using a holding pipette.

The conditions tested for electrofusion were the type of buffer, the pulse voltage, pulse duration and cell alignment. As illustrated in Table 1 below, the nonelectrolyte Zimmerman Cell Fusion Medium gave a higher fusion rate (8/9; 89%) than TL Hepes (1/9; 11%). No obvious difference was detected between pulses of 100 and 120 volts.

TABLE 1

| Fusion Medium | Pulse Voltage (40 microseconds) | Fused/Total | % Fusion |
| --- | --- | --- | --- |
| TL Hepes | 100 V | 0/5 | 0 |
| TL Hepes | 120 V | 1/4 | 25 |

TABLE 1-continued

| Fusion Medium | Pulse Voltage (40 microseconds) | Fused/Total | % Fusion |
| --- | --- | --- | --- |
| Zimmerman | 100 V | 5/5 | 100 |
| Zimmerman | 120 V | 3/4 | 75 |

Pulse durations of 20 and 40 microseconds gave equivalent fusion rates whereas 10 microseconds was not as effective as shown in Table 2.

TABLE 2

| Pulse Voltage | Pulse Duration (μ sec) | Fused/Total | % Fused |
| --- | --- | --- | --- |
| 100 V | 40 μ sec | 14/18 | 78 |
| 100 V | 20 μ sec | 15/19 | 79 |
| 100 V | 10 μ sec | 2/10 | 20 |

EXAMPLE 2

The development of embryos in which pronuclei were first removed and then reinserted was tested in vitro to test viability of nuclear-inserted bovine embryos. Of 29 such nuclear reinserted embryos, nine developed to 7- to 12-cells and 6 developed 4- to 6-cells, and the remainder were between 1 and 3-cells after in vitro culture for 48 hours.

Next, tests were done of actual nuclear transfers from donor embryo cells to pronuclear stage oocytes. Table 3, shown in two parts below, shows the development of nuclear transplant, and control embryos after development for five days in a sheep oviduct. Control embryos consisted of embryos recovered from cows on the same day and in most cases were transferred to the oviduct contralateral to nuclear transplant embryos.

TABLE 3

| Nuclear Donor | Cytoplasmic Recipient | Number Transf. | Total Number Recovered(%) | Empty Zona (%) |
| --- | --- | --- | --- | --- |
| Pronuclear | Pronuclear | 71 | 38 (54) | 9 (13) |
| Control | | 49 | 30 (61) | 0 (0) |
| 2, 4, or 8-cell | Pronuclear | 18 | 10 (56) | 3 (17) |
| Control | | 23 | 19 (83) | 0 (0) |

| Nuclear Donor | 1-3 Cell (%) | 4-6 Cell (%) | 7-9 Cell (%) | 10-16 Cell (%) | Morula or Blastocyst (%) |
| --- | --- | --- | --- | --- | --- |
| Pronuclear | 14 (48) | 3 (10) | 3 (10) | 2 (7) | 5 (17) |
| Control | 12 (40) | 2 (7) | 2 (7) | 3 (10) | 11 (37) |
| 2, 4, or 8-cell | 7 (100) | 0 (0) | 0 (0) | 0 (0) | 0 (0) |
| Control | 8 (42) | 1 (5) | 1 (5) | 1 (5) | 8 (42) |

(Percentages based on number of intact embryos recovered from sheep oviducts.)

Control embryos were pronuclear to eight-cell stage and were not necessarily the same stage as nuclear transplant embryos, therefore, direct comparisons could not be made between the cell stages attained. However, the control groups did indicate that the embryos survived and developed after being recovered from slaughtered animals, transported to the laboratory and maintained at room temperature for several hours. Pronuclear embryos in which nuclei were removed and reinserted also developed to morula or blastocysts in the sheep oviduct. Two of the embryos that developed from the pronuclear reinsertion were transferred to a recipient cow and both resulted in the birth of normal calves. Embryos in which pronuclei were replaced with nuclei from two, four or eight-cell embryos did not develop beyond one or two cleavage divisions.

Although all embryos were embedded in agar, most were recovered free of the agar blocks. Control embryos were all recovered intact; however, about 15% of the transferred micromanipulated embryos were recovered as empty zona pellucidae.

From these experiments it was determined that nuclei can be removed from pronuclear bovine cells and nuclear material inserted successfully. Cell fusion between nuclear cells and recipient oocytes was possible in a non-ionic media and was optimized if the membrane boundary between the donor cell and recipient oocyte was oriented perpendicular to the direction of the electric fusion pulse.

EXAMPLE 3

In this example, donor cells were selected to be 4- to 32-cell stage blastula embryos obtained at slaughter 2 to 5 days post estrus. Recipient oocytes were aspirated from 1-5 mm follicles obtained from abattoir-recovered ovaries matured in vitro 22 to 26 hours by the procedure of Critser et al. ("Influence of Cumulus Cell Association During In Vitro Maturation of Bovine Oocytes on Embryonic Development," *Biol. of Reprod.* 34:Suppl. 1 p. 192 (Abstract No. 286), 1986), or in vivo matured oocytes were recovered at slaughter 36 hours after onset of estrus. The recipient oocytes were stripped of cumulus oophorus by vortexing for 10 minutes in TALP-Hepes buffered medium containing 1 mg/ml bovine testes hyaluronidase.

In the procedure detailed above, the matured oocytes were enucleated, removing, in some cases, the polar body and only the adjacent cytoplasm, and, in other cases, about one-half of the cytoplasm. Enucleation and transfer were conducted in 7.5 micrograms per milliliter cytochalasin B. Donor blastomeres, with nuclei, were aspirated from the donor embryos and injected into the perivitelline space of the enucleated recipient oocytes. Activation and fusion were conducted by dielectrophoresis in Zimmerman Cell Fusion Medium, in the procedure described above. Post-fusion embryos were cultured 16-18 hours in modified Tyrodes medium prior to embedding in agar chips and transferring to the ligated oviduct of an ewe.

After five days of culture in vivo, the embryos were recovered and evaluated. Evaluation of the results indicated an increased efficiency of fusion where the recipient oocyte had about one-half of its cytoplasm removed and where the donor blastomere was from a 4- to 16-cell embryo. The efficiency for this recipient/donor combination was 237 out of 342, or 69% successful fusion. The efficiency of in vivo development to the morula or blastocyst stage was not significantly different regardless of whether the recipient oocyte was prepared by either method (3.7% and 1.9%). However, development to the morula or blastocyst stage was better for in vivo matured oocytes (27%) as compared to in vitro matured oocytes (1.9%) even when they had about one-half their cytoplasm removed. Apparently, the in vitro matured oocytes were not properly matured. The embryos which developed to the morula or blastocyst stages appeared normal in development. Fourteen of the morula or blastula stage embryos were transplanted non-surgically into the uteri of cattle at a suitable stage of estrus as is commonly done with embryo transplants. Pregnancies were initiated in the case of four embryos, which were carried in three maternal cows. Two of these resulted in the birth of normal calves. The remaining two embryos were aborted between days 25 and 90 of gestation.

From this example it appears that the transfer of the nuclei of 4- to 16-cell donor embryo cells to recipient oocytes can result in the creation of viable embryos and, ultimately, live births. These results suggest that nuclear transfer can be used to multiply genetically identical embryos so that producing herds of genetically identical cattle could become possible.

Although the foregoing invention has been described in some detail, it will be obvious that certain changes and modifications may be practiced within the scope of the claims.

We claim:

1. A method for transplanting a nucleus from a two to thirty-two cell donor bovine embryo to a recipient oocyte comprising the steps of:
   (a) isolating a membrane-bounded nucleus from a cell of the donor embryo;
   (b) removing the nuclear chromosomal material from the recipient oocyte (to prepare an enucleated recipient oocyte);
   (c) placing the donor membrane-bounded nucleus with its membrane adjacent to that of the enucleated recipient oocyte; and
   (d) electrically fusing the membranes of the membrane-bounded nucleus and the enucleated recipient oocyte together to form an embryonic single cell with a nucleus from the donor embryo.

2. The method according to claim 1 wherein the membrane-bound nucleus is a whole blastomere.

3. The method according to claim 1 wherein the membrane-bound nucleus is a karyoplast aspirated from a blastomere.

4. The method according to claim 1 further comprising, before step (d), orienting the membrane-bound nucleus and the enucleated recipient oocyte so that the plane of contact of their membranes is perpendicular to the direction of electric current flow in step (d).

5. The method according to claim 1 wherein said donor bovine embryo cell is from a four-cell to thirty two-cell embryo.

6. The method according to claim 1 wherein, prior to step (c), the membrane-bounded nucleus and the enucleated recipient oocyte are placed in a maintenance solution.

7. The method according to claim 6 wherein the maintenance solution is Hepes buffered modified Tyrodes medium.

8. The method according to claim 7 wherein said donor bovine embryo and said recipient oocyte are placed in a solution including cytochalasin B for approximately ten minutes prior to step (a).

9. The method according to claim 1 wherein the recipient oocyte is a metaphase II stage oocyte.

10. The method according to claim 1 wherein said recipient oocyte is enucleated by aspirating approximately one-half the cytoplasm juxtaposed to the polar body of said oocyte, leaving an enucleated one-half membrane-bounded oocyte.

11. The method according to claim 1 wherein said recipient enucleated oocyte includes a perivitelline space and the membrane-bounded nucleus is inserted into the perivitelline space of the enucleated oocyte.

12. The method according to claim 1 wherein step (d) is carried out in a fusion chamber consisting of two parallel electrodes on a glass slide.

13. The method according to claim 12 wherein, prior to step (d) said donor membrane-bounded nucleus and said enucleated recipient oocyte are placed in a non-ionic cell fusion medium.

14. The method according to claim 13 wherein said cell fusion medium is Zimmerman Cell Fusion Medium.

15. A method for producing cloned bovine embryos comprising:
    (a) isolating a nucleus, bounded by a membrane, from a single cell of a two to thirty-two cell donor bovine embryo;
    (b) enucleating a recipient oocyte;
    (c) introducing the donor membrane-bounded nucleus into the perivitelline space of the enucleated recipient oocyte;
    (d) electrically inducing cell fusion between the membrane bounding the donor nucleus and the enucleated recipient oocyte;
    (e) culturing in vitro the electrically induced fused embryo obtained in step (d); and
    (f) transferring the cultured embryo of step (e) to the oviduct of a recipient maternal animal.

16. The method according to claim 15 wherein step (a) comprises removing a single blastomere from the donor embryo with the whole blastomere serving as the membrane bounded donor nucleus.

17. The method according to claim 15 wherein step (a) comprises aspirating a membrane-bound karyoplast containing a nucleus from a cell of the donor embryo.

18. The method according to claim 15 wherein, prior to step (d), the membrane-bound nucleus and the oocyte are oriented with the plane of contact of their membranes in a selected orientation so that the electrical fusion pulse of step (d) may be applied perpendicularly to the direction of that boundary.

19. The method according to claim 18 wherein the membrane-bounded nucleus and the enucleated recipient oocyte are oriented by mechanical manipulation.

20. The method according to claim 15 wherein said embryo is cultured in vitro in step (e) for about 18 to 24 hours.

21. The method according to claim 15 wherein said donor bovine embryo is a 4-cell to 32-cell stage embryo.

22. The method according to claim 15 wherein the membrane-bounded nucleus is aspirated from a cell of the donor bovine embryo with a beveled, sharpened enucleation and transfer pipette.

23. The method according to claim 22 wherein the enucleation and transfer pipette has an outer diameter of about 25 to 35 micrometers.

* * * * *